United States Patent
Koob

(10) Patent No.: US 8,946,163 B2
(45) Date of Patent: Feb. 3, 2015

(54) CROSS-LINKED COLLAGEN COMPRISING METALLIC ANTICANCER AGENTS

(71) Applicant: MiMedx Group, Inc., Kennesaw, GA (US)

(72) Inventor: Thomas J. Koob, Kennesaw, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

(21) Appl. No.: 13/815,834

(22) Filed: Mar. 15, 2013

(65) Prior Publication Data

US 2014/0142041 A1 May 22, 2014

Related U.S. Application Data

(60) Provisional application No. 61/728,198, filed on Nov. 19, 2012.

(51) Int. Cl.
*A61K 47/48* (2006.01)

(52) U.S. Cl.
CPC ..... *A61K 47/48292* (2013.01); *A61K 47/48976* (2013.01); *A61K 47/48992* (2013.01)
USPC ......................................... 514/17.2; 530/356

(58) Field of Classification Search
CPC ....... A61K 8/64; A61K 31/00; A61K 31/337; A61K 31/7056; A61K 33/24; A61K 8/65
See application file for complete search history.

(56) References Cited

U.S. PATENT DOCUMENTS

| | | | |
|---|---|---|---|
| 4,847,049 A | 7/1989 | Yamamoto | |
| 6,129,757 A | 10/2000 | Weadock | |
| 6,166,184 A | 12/2000 | Hendriks et al. | |
| 6,503,244 B2 | 1/2003 | Hayman | |
| 6,565,960 B2 | 5/2003 | Koob et al. | |
| 6,716,895 B1 | 4/2004 | Terry | |
| 6,821,530 B2 | 11/2004 | Koob et al. | |
| 7,901,455 B2 | 3/2011 | Koob et al. | |
| 8,177,839 B2 | 5/2012 | Koob et al. | |
| 8,192,481 B2 | 6/2012 | King | |
| 8,367,148 B2 | 2/2013 | Greenhalgh et al. | |
| 2002/0019516 A1 | 2/2002 | Noff et al. | |
| 2003/0187515 A1 | 10/2003 | Hariri et al. | |
| 2003/0204023 A1 | 10/2003 | Koob et al. | |
| 2004/0048796 A1 | 3/2004 | Hariri et al. | |
| 2005/0142161 A1 | 6/2005 | Freeman et al. | |
| 2007/0160573 A1 | 7/2007 | Gengrinovitch | |
| 2008/0046095 A1 | 2/2008 | Daniel | |
| 2008/0161917 A1 | 7/2008 | Koob et al. | |
| 2008/0200992 A1 | 8/2008 | Koob et al. | |
| 2008/0233552 A1 | 9/2008 | Ma et al. | |
| 2009/0053290 A1 | 2/2009 | Sand et al. | |
| 2009/0216233 A1 | 8/2009 | Wiedrich et al. | |
| 2009/0287308 A1 | 11/2009 | Davis et al. | |
| 2010/0094318 A1 | 4/2010 | Li et al. | |
| 2010/0104539 A1 | 4/2010 | Daniel et al. | |
| 2010/0291182 A1 | 11/2010 | Palasis et al. | |
| 2010/0317677 A1 | 12/2010 | Hassel et al. | |
| 2011/0282447 A1 | 11/2011 | Niu et al. | |
| 2011/0282448 A1 | 11/2011 | Paulos et al. | |
| 2012/0189571 A1 | 7/2012 | Sengupta et al. | |
| 2013/0202676 A1 | 8/2013 | Koob et al. | |

FOREIGN PATENT DOCUMENTS

WO WO-87/00062 A1 1/1987

OTHER PUBLICATIONS

Konishi et al. In vivo anti-tumor effect through the controlled release of cisplatin from biodegradable gelatin hydrogel. J Control Release. Oct. 30, 2003;92(3):301-13.*
U.S. Appl. No. 13/815,736, filed Mar. 15, 2013, Koob.
U.S. Appl. No. 13/815,775, filed Mar. 15, 2013, Koob.
U.S. Appl. No. 13/860,473, filed Apr. 10, 2013, Koob.
U.S. Appl. No. 13/903,878, filed May 28, 2013, Koob.
U.S. Appl. No. 13/984,842, filed Feb. 13, 2012, Morse et al.
Hannallah et al., "Cerebrospinal Fluid Leaks Following Cervical Spine Surgery", J Bone Joint Surg Am, 2008;90(5):1101-1105.
International Search Report and Written Opinion for PCT Application No. PCT/US2012/065672, mailed Feb. 8, 2013.
International Search Report and Written Opinion for PCT Patent Application No. PCT/US2012/024814 mailed Aug. 16, 2012.
Khan et al., "Postoperative management protocol for incidental dural tears during degenerative lumbar spine surgery: a review of 3,183 consecutive degenerative lumbar cases", Spine, 2006; 31(22):2609-2613.
Koob et al., "Mechanical and thermal properties of novel polymerized NDGA—gelatin hydrogels", Biomaterials, 2003; 24(7):1285-1292.
Koob et al., "Material properties of polymerized NDGA—collagen composite fibers: Development of biologically based tendon constructs", Biomaterials, 23(1): 203-212, 2002.
Kostova, "Platinum Complexes as Anticancer Agents", Recent Patents on Anti-Cancer Drug Discovery, 2006; 1(1):1-22.
Mayfield et al., "Watertight closure of spinal dura mater: Technical note", Journal of Neurosurgery, 1975; 43(5):639-640.
Borkow et al., "Reducing the risk of skin pathologies in diabetics by using copper impregnated socks", Medical Hypotheses, 2009, 1-4, doi:10.1016/j.mehy.2009.02.050.
Lu et al., "Molecular mechanisms and clinical applications of nordihydroguaiaretic acid (NDGA) and its derivatives: An update," Med. Sci. Monit., (2010), 16(5):RA93-RA100.
Kelly et al., "Disparate Effects of Similar Phenolic Phytochemicals as Inhibitors of Oxidative Damage to Cellular DNA", Mutation Res., vol. 485, pp. 309-318, (2001).
PCT International Search Report and Written Opinion dated Apr. 16, 2014 in related PCT Patent Application No. PCT/US13/67622.

* cited by examiner

*Primary Examiner* — Karlheinz R Skowronek
*Assistant Examiner* — Jia-Hai Lee
(74) *Attorney, Agent, or Firm* — Foley & Lardner LLP

(57) ABSTRACT

The disclosure describes collagen constructs comprising anticancer agents, preferably, platinum, and related methods.

11 Claims, 2 Drawing Sheets

CROSS-LINKED COLLAGEN COMPRISING METALLIC ANTICANCER AGENTS

CROSS-REFERENCE TO RELATED APPLICATIONS

This application claims priority to U.S. provisional patent application No. 61/728,198, filed on Nov. 19, 2012. The content of the prior application is incorporated herein by reference in its entirety.

FIELD OF THE INVENTION

This invention relates to cross-linked collagen constructs comprising metal containing anticancer agents or metallic anticancer alkylators, preferably alkylators comprising platinum, and related methods.

BACKGROUND OF THE INVENTION

Koob et al. have described methods of producing nordihydroguaiaretic acid (NDGA) polymerized collagen fibers for various biomedical applications, some with tensile strengths similar to that of natural tendon (e.g., about 91 MPa). See, for example, Koob and Hernandez, *Material properties of polymerized NDGA-collagen composite fibers: development of biologically based tendon constructs*, Biomaterials 2002 January; 23 (1): 203-12; and U.S. Pat. No. 6,565,960, the contents of which are hereby incorporated by reference as if recited in full herein.

SUMMARY OF THE INVENTION

This invention is directed to cross-linked collagen constructs, preferably which are biocompatible, comprising a releasable metal-containing anticancer agent incorporated thereto. The constructs can be used for in vivo delivery and, in some embodiments, the anticancer agent is incorporated into the construct so that there is a sustained release of the anticancer agent.

In one aspect of this invention, the biocompatible cross-linked collagen is provided as a construct with a releasable anticancer agent and, preferably, a platinum anticancer agent. Such constructs provide the beneficial properties of the cross-linked collagen as well as impart anticancer properties to the construct.

In another aspect, the biocompatible cross-linked collagen construct provides a sustained release of the anticancer agent including an immediate release, an intermediate release and an extended release. In certain embodiments, the anticancer agent is continuously released from the collagen construct.

In one aspect, provided herein is an anticancer cross-linked collagen construct comprising:
a cross-linked collagen comprising collagen and one or more cross-linking agents and
an anticancer amount of platinum incorporated into the construct at least in part through the cross-linking agent.

As used herein, "incorporated" or "bound" refers to the metal being covalently and/or non-covalently, such as via cation-pi interactions, attached to the construct, and includes multiple covalent bonds or chelates between the metal atom and the construct.

In one embodiment, the cross-linking agent comprises a 1,2-benzoquinone and/or a 1,2-dihydroxy phenyl moiety. In another embodiment, the platinum is chelated at least in part to the benzoquinone and/or the 1,2-dihydroxyphenyl moiety. In another embodiment, the cross-linking agent is selected from the group consisting of nordihydroguaiaretic acid (NDGA), 3,4-dyhydroxyphenylalanine, dopamine, 3,4-dihydroxybenzaldehyde, 3,4-dihydroxybenzoic acid, a carbodiimide, glutaraldehyde or another di- or multi aldehyde, formaldehyde, tannic acid, isocyanates, pluronics, and epoxy resins. In another embodiment, the cross-linking agent is NDGA. In another embodiment, the platinum comprises platinum (II) and/or platinum (IV). In another embodiment, the platinum comprises cis-(NH$_3$)$_2$Pt(II),

(II)

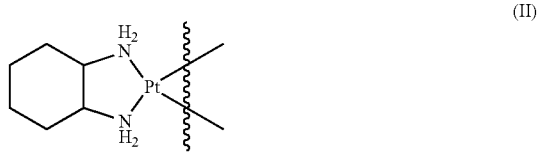

(II)

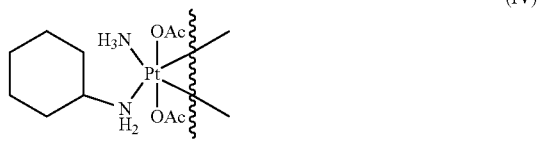

(IV)

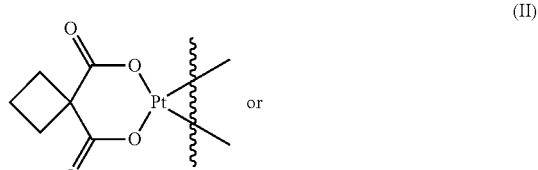

(II)

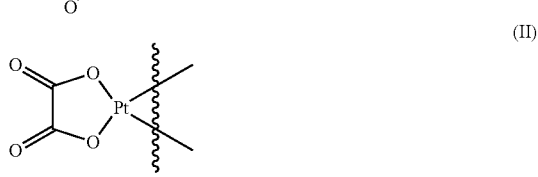

(II)

wherein

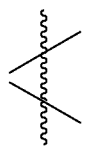

denotes binding to the cross-linked collagen construct. In another embodiment, the platinum incorporated into the construct is present in an amount of between about 0.1% to about 30%.

In another embodiment, the anticancer amount of platinum is released in vivo in contact with an aqueous medium. In another embodiment, the anticancer cross-linked collagen construct provides a sustained release of platinum, wherein the sustained release comprises a plurality of release rates including an immediate release, an intermediate release, an extended release or any combination of release rates thereof. In another embodiment, an effective amount of platinum is released from about 1 minute to about 60 days, or any range therein.

As used herein, an "anticancer amount of platinum" refers to an amount of platinum incorporated into the anticancer cross-linked collagen construct of this invention that when contacted in vitro or in vivo with cancer cells inhibit or kill cancer cells or tissue, and inhibits or kills, preferably, 50%, more preferably, 90%, and still more preferably 99% of such cells or tissue. As used herein, "effective amount of platinum" refers to an amount of platinum that is, preferably, released from an anticancer cross-linked collagen construct of this invention and that is sufficient to inhibit or kill, in vitro or in vivo, preferably, 50%, more preferably, 90%, and still more preferably 99% of cancer cells or tissue. An effective amount of platinum can improve one or more cancer symptoms, and/or ameliorate one or more cancer-side effects, and/or prevent and/or impede invasiveness and/or metastasis of cancer. In certain embodiments, an anticancer amount of platinum can differ from an effective amount of platinum.

As used herein "cancer amenable to treatment with platinum alkylators" refer to those cancers that are treated with one or more platinum alkylators, non limiting examples of which include cisplatin, carboplatin, oxaliplatin, satraplatin, as are well known to the skilled artisan. Non limiting examples of such cancers include non-small cell lung, breast, ovarian, testicular, and bladder cancer. "Alkylators" or "alkylating agents" as used herein are agents that can alkylate, or transfer an electrophilic metal moiety, such as a platinum moiety to, nucleic acids and/or proteins as is well known to the skilled artisan.

In one embodiment, the invention is directed to a construct comprising a cross-linked collagen construct and an anticancer amount of platinum incorporated into the construct to provide an anticancer, cross-linked collagen construct. In certain aspects, the cross-linked collagen construct is cross-linked with one or more cross-linking agent selected from the group consisting of nordihydroguaiaretic acid (NDGA), cross linkers including 2-9 1,2-dihydrophenyl moieties, 3,4-dihydroxyphenylalanine, dopamine, 3,4-dihydroxybenzaldehyde, 3,4-dihydroxybenzoic acid, a carbodiimide, glutaraldehyde and another dialdehyde and a multialdehyde, formaldehyde, tannic acid, isocyanates such as di and multi-isocyanates, alpha-diazo pyruvates such as di and multi-alpha-diazo pyruvates, pluronics, preferably such as L61, L121, F68, F108, and epoxy resins. In exemplary embodiments, the cross-linked collagen construct is at least cross-linked with NDGA.

In yet another embodiment of the invention, the platinum incorporated into the construct is bound to a quinone group and/or a catechol group present in the cross-linked collagen construct. In other embodiments of the invention, the platinum incorporated into the construct may be bound to a basic nitrogen atom, non limiting examples of which include amino, or mono- or di-alkylated amino, and imidazole. In certain aspects, the platinum is platinum (+2) and/or platinum (+4). In certain preferred aspects, the platinum anticancer agent comprises a cis diamino platinum moiety. As used herein the amino refers to ammonia or a cycloalkyl amine, or a heteroaryl or a heterocyclyl amine, where the platinum coordinating nitrogen atom can be a part of the ring system or derivative the ring system. Examples of cis diamino platinum moieties and other platinum moieties useful in this invention are described, e.g., in Kostova, Recent patents on Anti-Cancer Drug Discovery, 2006, 1, 1-22, which is incorporated herein in its entirety by reference. In other aspects, the platinum incorporated into the construct is present in an amount of between about 0.1% to about 30%.

In additional aspects of the invention, the anticancer amount of platinum is released in vivo, e.g., during degradation of the construct. In certain aspects, the anticancer, cross-linked collagen construct provides a sustained release of platinum, wherein the sustained release comprises a plurality of release rates including an immediate release, an intermediate release, an extended release or any combination of release rates thereof. In other aspects, the plurality of release rates are adjusted to provide a suitable range of release rates, wherein the range of release rates comprises from about 1 minute to about 60 days, or any range therein.

The anticancer collagen constructs can be formulated variously depending on their mode of delivery and their delivery site. In certain preferred embodiments, the anticancer collagen constructs are powdered or micronized. In some embodiments, the powdered or micronized constructs are compacted into a shape such as a pellet or an implant shaped as the graphite tube in a pencil. Unit lengths or doses of such shaped solid dosage forms are also provided. Such solid forms of the anticancer constructs can be administered topically to a site needing anticancer treatment, or may be administered into a patient by using dry, solid injection techniques well known and/or commercially available, or their obvious modifications. Non-limiting examples of such solid injections techniques include, the Glide SDI, solid injection system.

In other embodiments, the anticancer collagen constructs or their powdered or micronized or other forms are formulated as a viscous fluid. Such viscous formulations may preferably include non-aqueous organic liquids, which can include polymers such as polyethylene glycols, Polaxamer® polymers, and the like, and/or small molecule organic solvents. Such viscous formulations may be administered, preferably site specifically, using high pressure syringes that are well known and/or commercially available, or obvious modifications thereof. Non limiting examples of such high pressure syringes include those described in U.S. Pat. No. 6,503,244 (incorporated herein by reference) and the likes.

In another aspect, provided herein is a method of manufacturing an anticancer cross-linked collagen construct comprising cross-linked collagen and an anticancer amount of platinum, wherein the platinum is incorporated into the construct at least in part through the cross-linking agent, the method comprising providing the cross-linked collagen comprising collagen and one or more cross-linking agents; and contacting the cross-linked collagen with a cis-diaqua or a cis-dihalo platinum complex, to provide the anticancer cross-linked collagen construct.

As used herein, a cis-diaqua platinum complex contains 2 water molecules bound to platinum in cis or adjacent configuration, and a cis-dihalo platinum complex contains 2 halogen, preferably chloride groups, bound to platinum in cis or adjacent configuration.

Another embodiment of the invention is directed to a method of manufacturing a construct comprising: providing a cross-linked collagen; and contacting the cross-linked collagen construct with an anticancer amount of platinum to chemically bind the platinum to the cross-linked collagen construct to provide a therapeutically effective amount of anticancer platinum in the construct, thereby producing an anticancer cross-linked collagen construct.

In another aspect, provided herein is a method of treating a subject suffering from cancer amenable to treatment with platinum alkylators, the method comprising administering an anticancer cross-linked collagen construct in the subject, wherein the construct comprises (a) cross-linked collagen comprising collagen and one or more cross-linking agents and (b) platinum incorporated therein at least in part through the cross-linking agent, to administer an effective amount of platinum into the subject.

In yet another embodiment, the invention is directed to a method of treating a subject in need of treatment for a cancer treatable with a platinum anticancer agent, comprising: a) implanting a medical construct in a subject, wherein the medical construct comprises cross-linked collagen and an anticancer amount of platinum incorporated therein to provide a therapeutically effective amount of anticancer platinum in the construct, and b) releasing the anticancer agent from the construct in a plurality of in vivo release rates, thereby inhibiting cancer. In one embodiment the effective amount of platinum is released from the construct in a plurality of in vivo release rates. Methods of determining the therapeutically effective amount, appropriate mode of administration of the compounds and compositions provided herein will be apparent to the skilled artisan upon reading this disclosure and based on other methods known to them.

It is noted that aspects of the invention described with respect to one embodiment, may be incorporated in a different embodiment although not specifically described relative thereto. That is, all embodiments and/or features of any embodiment can be combined in any way and/or combination. These and other objects and/or aspects of the present invention are explained in detail in the specification set forth below.

DETAILED DESCRIPTION

Figure 1:
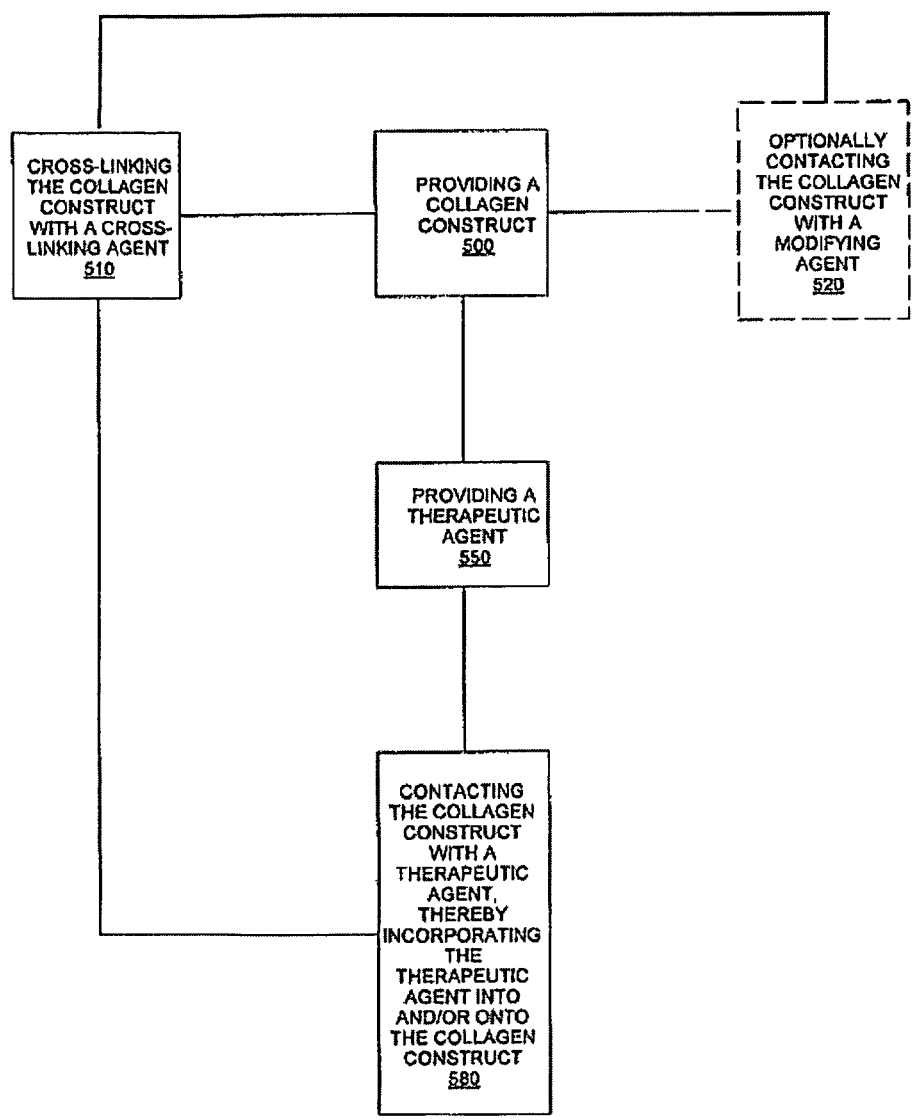
FIG. 1 is a flow chart of operations that can be used to carry out embodiments of the present invention. Preferably, the collagen construct incorporating the therapeutic agent is a collagen construct comprising platinum as provide herein.

The present invention is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Before describing this invention, the following terms are defined.

DEFINITION

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Collagen construct," as used herein, refers to a device and/or material that comprises biocompatible cross-linked collagen. The collagen construct can be in finished or final form for use or in an unfinished or pre-final form. The collagen constructs of the present invention can comprise natural collagen, natural collagenous tissue, synthetic collagen, and/or any combination thereof "Synthetic collagen" as used herein, refers to collagen material that has been formed and/or chemically and/or physically created or altered from its naturally-occurring state. As such, synthetic collagen may include, but is not limited to, collagen material in the form of a gel, gelatin, fibril, slurry, hydrogel or a film, each of which is discussed in further detail herein below.

The term "cross-linked collagen construct" or "biocompatible cross-linked collagen construct" refers to collagen cross-linked with a cross-linking agent that is preferably biocompatible and capable of binding and releasing a metallic anticancer agent. In one embodiment, the cross-linking agent contains two or more functionalities which are reactive with collagen as well as one or more functionalities which are capable of binding and releasing the metallic anti-cancer agent. "Anticancer cross-linked collagen construct" refers to a cross linked collagen construct further comprising an anti-cancer agent, preferably, a metallic anti-cancer agent, more preferably, platinum.

In one embodiment, the cross-linking agent contains the same or different functionalities which can both cross-link collagen and reversibly bind the anticancer agent. Preferably, the cross-linking agents are catechol containing cross-linking reagents including, by way of example, NDGA as well as:

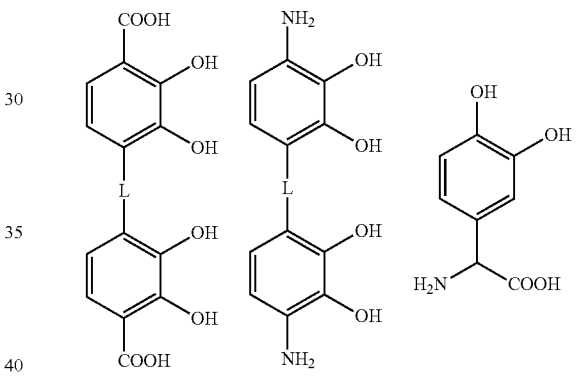

where L is a covalent bond or a linking group of from 1 to 10 atoms which comprise 1-8 carbon atoms and 0 to 4 heteroatoms selected from the group consisting of oxygen, sulfur, NH, and the like.

Such catechol containing cross-linking reagents permit a variety of lengths between the collagen fibrils as well as binding to different functionalities. In one exemplary embodiment, the catechol cross-linking reagent is NDGA, which is well known in the art.

"Cross linkers including 2-9 1,2-dihydroxyphenyl moieties" refer to, in preferred embodiments, compounds of formula:

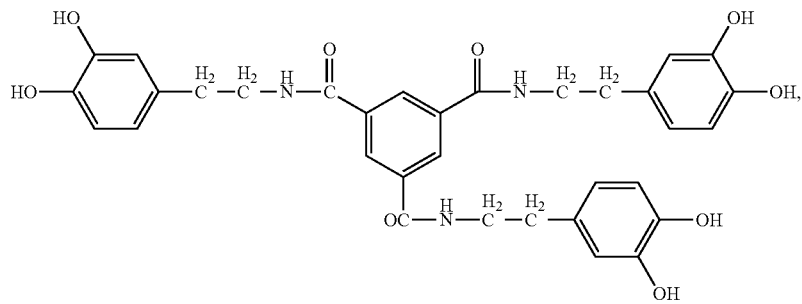

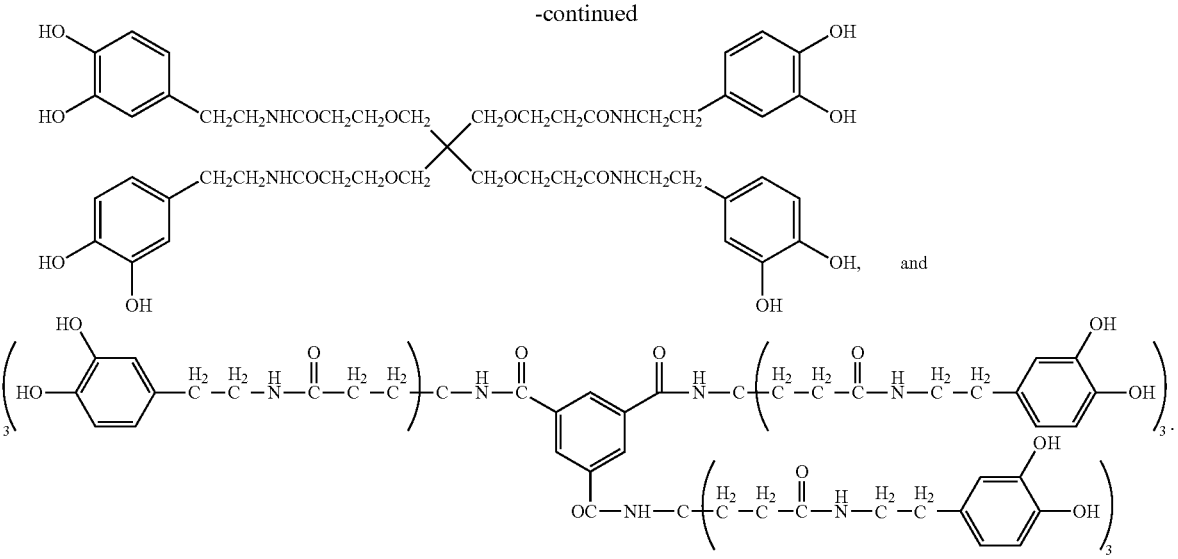

In some embodiments, the phenyl ring containing one or more hydroxy groups can further contain alkylthio (alkyl-S—) and/or amino, or in some embodiments, the hydroxy groups in the phenyl ring can be replaced by alkylthio (alkyl-S—), cyano, and/or amino, groups. In some embodiments, the phenyl ring or the hydroxy substituted phenyl ring can be replaced by a heteroaryl ring containing one or more nitrogen atoms, preferably (—N=) nitrogen atom(s), that can bind the metal. Such other substituted phenyl or heteroaryl compounds are made according to methods well known to a skilled artisan.

In some embodiments, the chelators are bis amino acids where the two amino acid moieties are covalently bonded by a linker such as L. The amino acid moieties are suitable modified so as to bind to collagen, as will be well know to a skilled artisan. For example, and without limitation, aspartic acid, and/or glutamic acid can be useful as the two amino acids.

By including a variety of ligands that bind the anti-cancer metal, preferably platinum, strongly to weakly, the release rate of that metal can be controlled.

Such other cross-linkers will be apparent to the skilled artisan upon reading this disclosure.

A "carbodiimide" refers to a compound of formula X—N=C=N—X, wherein each X independently is $C_1$-$C_6$ alkyl optionally substituted with 1-2 dialkylamino groups, or is $C_5$-$C_6$ cycloalkyl.

"$C_m$" when placed before a group refers to that group containing m carbon atom(s).

"Alkyl" refers to a hydrocarbyl radical, preferably monovalent, containing 1-12 carbon atoms. Non limiting examples of alkyl includes methyl, ethyl, propyl, isopropyl, butyl, isobutyl, tertiary butyl, and the like.

"Cycloalkyl" refers to a cyclic hydrocarbyl radical, preferably, monovalent, containing 3-10 carbon atoms and includes bicyclic radicals. Non limiting examples of cycloalkyl include cycloproyl, cyclobutyl, cyclopentyl, cyclohexyl, and the like.

"Dialdehyde" refers to a compound of formula OHC-L-CHO, wherein L is defined as above. "Multialdehyde" refers to a compound of formula:

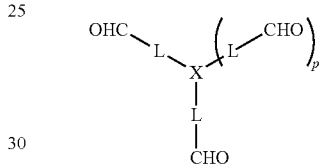

wherein, each L independently is defined as above, p is 1-9, and X is defined as follows. X can be a moiety containing one or more, preferably, 1-9, 1,2-dihydroxyphenyl moiety. Or, X can be nitrogen, is an hydrocarbyl moiety optionally containing 1-10 heteroatoms, or is a glycosidic moiety or an amino acid and such other multifunctional moiety to which the L groups are bound. Dialdehydes and multialdehydes are well known to the skilled artisan.

"Di-isocyanate" refers to a compound of formula ONC-L-CNO, wherein L is defined as above. "Multi-isocyanate" refers to a compound of formula:

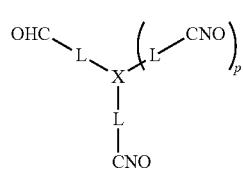

wherein X, L, and p are defined as above. Di-isocyanates and multi-isocyanates are well known to the skilled artisan.

"Di-alpha-diazo pyruvate" refers to a compound of formula $N_2C(O)C(O)$-L-$C(O)C(O)N_2$, and "multi-alpha-diazo pyruvate" refers to a compound of formula:

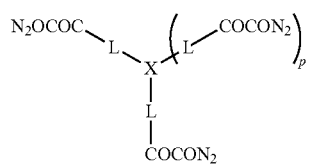

wherein X, L, and p are defined as above. Di-alpha-diazo pyruvates and multi-alpha-diazo pyruvates are well known to the skilled artisan.

"Pluoronics" refers to block copolymers of formula: $HO(C_2H_4O)_a(CH_2CH(CH_3)O)_b(C_2H_4O)_aH$ where such polymers and values of a and b are well known to the skilled artisan.

Exemplary biocompatible cross-linked collagen constructs (which are sometimes referred to herein as "collagen constructs" or merely "constructs"), include, but are not limited to, patches, such as wound bed patches, muscle or organ patches, cardiac patches, hernia patches, skin patches, burn treatment patches, and skin/tissue repair patches; cuffs; blood vessel (artery, vein, and the like) repair material; valve replacements or valve repair material; auto-graft material; allo-graft material; xenograft material; nerve guides; tubes; tendon sleeves, such as sleeves that can reside about repairing tendon to prevent or inhibit adhesions; indwelling tubes for delivery of anticancer agents; ducts, such as lymphatic, hepatic, pancreatic and cystic ducts; tubes, such as ureter and urethra tubes; collagen fiber; collagen gel; sutures; cords; twisted cords; ligament and/or tendon prosthesis; cables; braids; ribbons; staples; rivets; sponges; and the like. Further examples and description of devices are described in U.S. Pat. No. 7,901,455; U.S. Patent Application Publication Nos. 2008/0161917, 2008/0188933, 2008/0200992, 2009/0216233, 2009/0287308, 2010/0094318, and 2010/0094404; U.S. patent application Ser. Nos. 13/153,665 and 13/105,353; and U.S. Provisional Patent Application No. 61/450,179, which are incorporated herein by reference.

The collagen constructs of the present invention can be dry or partially hydrated. The term "dry" as used herein means the construct has a moisture content of less than about 5% by weight of the construct. The term "partially hydrated" as used herein means that the construct has a moisture content that is less than about 50%, typically less than about 75% of the moisture content at full hydration, measured ex vivo after 24 hours in a saline bath at ambient conditions. Thus, the construct can have a moisture content of less than about 25% by weight of the construct, such as less than about 15% by weight of the construct. In certain embodiments, the construct comprises at least one dry manufactured collagen fiber.

In some embodiments of the present invention, the collagen construct comprises at least one collagen fiber. A collagen fiber can be an elongate continuous length of fiber formed of denatured (gelatin) and/or non-denatured collagen (e.g., whole or fragmented native collagen fibers from tendon, skin, or other sources). An elongate collagen fiber can have a length of at least about 0.25 inches (0.63 cm), typically greater than about 0.5 inches (1.27 cm), such as between about 1-30 inches (2.54 cm to 76.2 cm) or between about 1 m to about 100 m. In some embodiments of the present invention, a collagen construct comprises a plurality of elongate NDGA cross-linked collagen fibers. In certain embodiments of the present invention, a collagen construct comprises at least one polymerized elongate collagen fiber.

Examples of fiber configurations include a single fiber, a plurality of fibers, a fiber bundle, or a plurality of fiber bundles and/or fibers twisted, woven or braided that define a twisted, woven or braided fiber bundle and/or fiber construct.

The term "patch" refers to a piece or segment of biomaterial that can be placed on and/or affixed to target anatomical structure, typically soft tissue, to treat, protect, repair and/or reinforce a target site. The patch can be any geometric shape but is typically substantially planar and may, in position, conform to the shape of underlying or overlying tissue.

The term "implantable" and derivatives thereof means the device can be inserted, embedded, grafted or otherwise acutely or chronically attached or placed in or on a subject.

The terms "winding" and "wound" and derivatives thereof means to wrap about an object or center at least once, typically repeatedly, e.g., to turn in a series of circular motions. In some embodiments, at least one collagen fiber (multiple fibers, one or more fiber bundles) turns or rotates its circumferential position about a centerline or long axis. The winding may define a coil (e.g., a series of connected typically substantially concentric rings or spirals), woven and/or braided fiber arrangement with a number of revolutions or turns about a core and/or tube, typically in a regular pattern (but an irregular pattern may also be used) about a length of at least one layer of a tube or cylindrical shape.

The present invention finds use in medical applications and animal studies. The term "medical" includes both human and veterinary uses. Suitable subjects of the present invention include, but are not limited to avians and mammals.

In particular embodiments, the subject is "in need of" the methods of the present invention, e.g., the subject may benefit from a surgical procedure implanting a collagen construct of the present invention, such as a prosthesis or other device. In certain embodiments, after implantation, the collagen constructs of the present invention can confer a therapeutic and/or prophylactic effect to the subject, such as prevent a disease and/or clinical symptom, reduce the severity of a disease and/or clinical symptom relative to what would occur in the absence of the methods of the prevent invention, and/or delay the onset and/or progression of a disease and/or clinical symptom. The methods of the present invention can provide complete and/or partial treatment and/or protection. In particular embodiments, after implantation in or administration to a subject, the collagen constructs of the present invention treat and/or inhibit and/or protect against cancer, preferably, those that are treated with platinum anticancer agents, in the subject.

I. Anticancer Agents

Embodiments of the present invention are directed to biocompatible cross-linked collagen constructs with chemically bound anticancer agents for in vivo delivery at different release rates over time for medical use.

The collagen constructs of the present invention, in particular embodiments, can provide a therapeutically effective amount of an anticancer agent. "Therapeutically effective amount," as used herein, refers to an amount of an anticancer agent that elicits a therapeutically useful response in treating an existing medical condition and/or preventing or delaying the onset of a medical condition from occurring in a subject. In particular embodiments, the collagen construct provides a therapeutically effective amount of an anticancer agent for at least about 5 days, such as at least about 15 days, at least about 20 days, at least about 30 days, at least about 60 days, at least about 100 days, or more. In other embodiments, the collagen construct provides a therapeutically effective amount of an anticancer agent for the lifetime of the collagen construct. As used herein, the term "lifetime of the collagen construct" is the period of time beginning substantially when the collagen construct is implanted and extending until the time the collagen construct is removed or degrades, breaks down, delaminates, denatures, resorbs, absorbs, decomposes, or disintegrates, such that the collagen construct no longer serves its structural and/or functional purpose (i.e., the useful lifetime). In some embodiments of the present invention, an anticancer agent is released before, during, after, or upon degradation of the construct, or any combination thereof.

In some embodiments, the anticancer agent comprises an anticancer heavy metal cation. In certain embodiments, the anticancer agent is platinum. The term "platinum," as used herein, includes all platinum salts such as, platinum (+2), and or (+4) salts, preferably, platinum (+2) salts, still more preferably cis-diamino platinum salts. Accordingly, it is understood that all forms of anticancer platinum salts are contemplated to be suitable to provide a therapeutically effective dose of anticancer platinum according to the collagen constructs of the present invention.

The anticancer agent can present in a collagen construct of the present invention in an amount of between about 0.1% to about 30%, such as between about 0.1% to about 10%, about 1% to about 5%, about 1% to about 30%, about 3% to about 25%, or about 5% to about 15% by weight of the collagen construct. In some particular embodiments of the present invention, the anticancer agent is present in an amount of about 1% to about 5% by weight of the collagen construct.

The platinum can be present in the collagen construct in an amount between about 10,000 μg to about 300,000 μg, on average, or any range therein, such as about 10,000 μg to about 200,000 μg, about 15,000 μg to about 80,000 μg, about 20,000 μg to about 50,000 μg, or about 50,000 μg to about 150,000 μg per gram of the collagen construct, on average. In particular embodiments of the present invention, the heavy metal is present in an amount of about 15,000 μg to about 50,000 μg per gram of the collagen construct, on average.

The amount of the anticancer agent present in a collagen construct can be based on the weight of the collagen construct. In particular embodiments, the amount of the anticancer agent present in a collagen construct can be based on the dry weight of the collagen construct (i.e., having a moisture content of less than about 5% by weight of the construct). In other embodiments, the amount of the anticancer agent present in a collagen construct can be based on the weight of the collagen construct having a low moisture content (i.e., having a moisture content of less than about 25% by weight of the construct, such as less than about 15% by weight of the construct).

The anticancer agent can be incorporated into and/or onto the collagen constructs of the present invention. "Incorporate" and grammatical variants thereof, as used herein, refer to an anticancer agent being present in the collagen constructs of the present invention. The term "incorporate" and grammatical variants thereof, is intended to include embodiments where the anticancer agent is present on one or more of the surfaces of the collagen construct and/or present in one or more layers of the collagen construct. "Incorporate" is intended to include embodiments where an anticancer agent is bound to the collagen construct, such as through specific and/or nonspecific types of binding. Exemplary types of chemical bonds through which the anticancer agent can bind to the collagen construct include, but are not limited to, covalent bonds, noncovalent bonds, ionic bonds, metallic bonds, or any combination thereof. In some embodiments of the present invention, the anticancer agent can bind to and/or complex with the collagen and/or other materials or compounds in the collagen constructs of the present invention. In certain embodiments, the anticancer agent nonspecifically binds to the collagen construct to provide an immediate bolus release of the anticancer agent from the collagen construct and specifically binds to the collagen construct to provide a sustained release of the anticancer agent from the collagen construct. In other embodiments, the release of the anticancer agent from the collagen construct can be due to a combination of specific and nonspecific binding of the anticancer agent to the collagen construct.

In particular embodiments of the present invention, the anticancer agent can bind to and/or complex with a moiety or group present in the collagen construct. In some embodiments, the anticancer agent can bind to and/or complex with a moiety or group present in cross-linked collagen, e.g., NDGA cross-linked collagen, in the collagen constructs of the present invention. "Moiety" and "group" are used interchangeably herein to refer to a portion of a molecule present in the collagen construct, typically having a particular functional and/or structural feature, e.g., a linking group (a portion of a molecule connecting two other portions of the molecule). Exemplary functional groups include, but are not limited to, amino, sulfhydryl, carbonyl, hydroxyl, alkoxy, carboxyl, silyl, silyloxy, hydrocarbyl, cycloalkyl, aryl, thio, mercapto, imino, halo, cyano, nitro, azido, sulfoxy, phosphoryl, oxy, quinone, catechol, and the like. In particular embodiments, the functional group is a quinone and/or a catechol.

"Quinone," as used herein refers to a compound similar to 1,4-benzoquinone and derivatives thereof with one or more carbonyl group(s) in an unsaturated ring (Scheme 1). Exemplary quinones include, but are not limited, to 1,4-benzoquinone, 1,2-benzoquinone, 1,4-naphthoquinone, 9-10-anthraquinone, acetimidoquinone, alizarin, alkannin, 1-aminoanthraquinone; anthrimide, chimaphilin, chloranil, 2,6-dimethoxyquinone, duroquinone, emodin, fusarubin, 2-methylanthraquinone, menadione, oosporein, parvaquone, perezone, plumbagin, rhodoquinone, rufigallol, rufigallol, terreic acid, ubiquinones, aurantiogliocladin, nitranilic acid, and any combination thereof.

Scheme 1: Exemplary quinones.

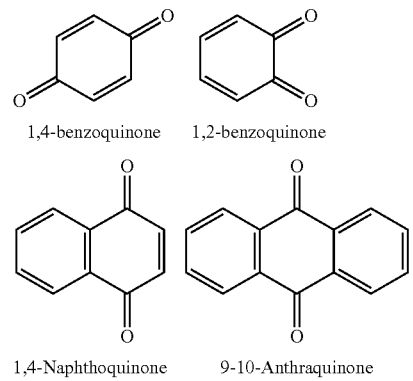

1,4-benzoquinone    1,2-benzoquinone 1,4-Naphthoquinone    9-10-Anthraquinone

"Catechol," as used herein, refers to a compound similar to 1,2-benzenediol and derivatives thereof with one or more hydroxyl group(s) in an unsaturated ring (Scheme 2). Exemplary catechols include, but are not limited to, 1,2-benzenediol, 2,3-dihydroxynaphthalene, 1,3-benzenediol, nordihydroguaiaretic acid, adrenalone, catechin, nitrocatechol, 3,4-dihydroxybenzaldehyde, 3,4-dihydroxybenzoic acid, deoxyepinephrine, dobutamine, dopamine, dopexamine, epinephrine, nordefrin, 3-pentadecylcatechol, tiron, and any combination thereof.

Scheme 2: Exemplary catechols.

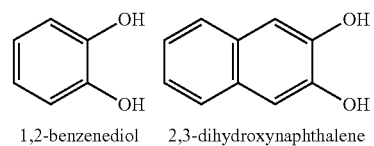

1,2-benzenediol    2,3-dihydroxynaphthalene

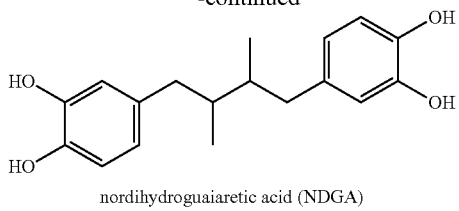

nordihydroguaiaretic acid (NDGA)

If the collagen construct comprises a quinone group and/or a catechol group, the anticancer agent can bind to and/or complex with the quinone group and/or catechol group. Exemplary anticancer agents that can bind and/or complex with a quinone and/or a catechol group, include, preferably platinum, (including its combined forms such as salts and complexes with carriers), anions such as chloride, oxoanions, and hyperoxide. A catechol can oxidize to a quinone and a quinone can be reduced to a catechol. In some embodiments of the present invention, upon or during the binding of a anticancer agent, a catechol group can be oxidized to a quinone or a quinone can be reduced to a catechol. In particular embodiments of the present invention, the anticancer agent is an anticancer agent, e.g., platinum, that binds to and/or complexes with a quinone and/or a catechol group present in the collagen construct. In some embodiments, a quinone and/or catechol group is present in the collagen construct as a result of the collagen construct being polymerized with a cross-linking agent, such as NDGA.

The crosslinked collagen-Pt constructs of this invention are prepared by contacting appropriate Pt salts, preferably, Pt(II) salts with a crosslinked collagen. Preferably, the Pt salt is a cis diamino Pt(II) dichloro or, yet more preferably, a cis diamino Pt(II) diaqua salt. An illustrative and non-limiting example is shown below:

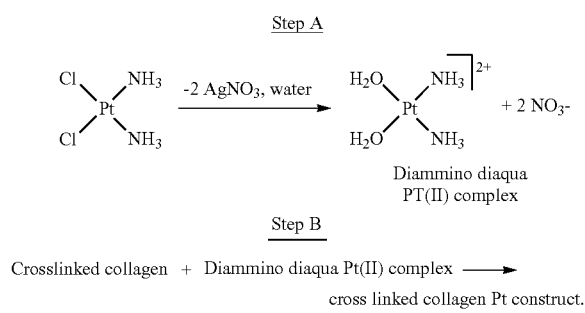

Excess Pt salts, not bound to the crosslinked collagen, can be removed by complexed with a resin, such as Chelex. A crosslinked collagen-Pt(II) construct can be converted to the corresponding Pt(IV) construct by oxidation, for example with $H_2O_2$.

In some embodiments of the present invention, the collagen construct is treated with an agent to modify the collagen construct's ability to incorporate an anticancer agent. In particular embodiments, the agent modifies or adds a functional group present in the collagen construct to increase and/or enhance the incorporation of an anticancer agent into and/or onto the collagen construct. Exemplary types of reactions through which a modification can be made include, but are not limited to, redox reactions, substitution reactions, addition reactions, elimination reactions, rearrangement reactions, biochemical reactions, and any combination thereof. In particular embodiments, a redox reaction is performed to modify and/or change the oxidation state of a functional group present in the collagen construct, e.g., a quinone group and/or a catechol group. In certain embodiments, the agent can be a polymerizing agent, such as, but not limited to, NDGA. In other embodiments, the agent blocks (e.g., partially or completely) a functional group present in the collagen construct, which optionally can subsequently be unblocked, to allow for one or more anticancer agents and/or other materials to be incorporated into and/or onto the collagen construct.

In certain aspects, the greater the affinity of the anticancer agent for the collagen construct, the more stable the coordination of the composition due to the ionic interaction between the anticancer agent and the collagen construct. Conversely, the lower the affinity of the anticancer agent for collagen construct, the less stable the coordination of the composition. Thus, for applications where it is desired to provide a slower, faster or combination of release rates of the anticancer agent sequestered in the collagen construct, the binding affinity of the anticancer agent can be modified to achieve the desired release rate(s) using the methods disclosed herein.

In various embodiments, it is contemplated that at least three affinity phases correlating to release rates can be achieved: (1) a mobile phase; (2) low affinity phase; and (3) high affinity phase, wherein the phases are arranged by order of increasing affinity of the anticancer agent for the collagen construct. In one aspect, the mobile phase correlates to unbound and/or weakly bound anticancer agent to the collagen construct. In another aspect, the low affinity phase correlates to non-specific and specific binding of the anticancer agent to moieties or groups present in the collagen construct. In another aspect, the high affinity phase correlates to binding of the anticancer agent to quinone and/or catechol groups present in the collagen construct.

It is to be understood that various binding affinities can be achieved using the methods disclosed herein depending on the desired release rate(s). In an exemplary embodiment, a plurality of release rates can be achieved by introducing an anticancer agent, for example, platinum, onto a cross-linked collagen construct, such that the anticancer agent is incorporated into and/or onto the collagen construct via a mobile phase, low affinity and high affinity phase. In some aspects, the utilization of different affinities of the anticancer agent will allow the skilled artisan to make a collagen construct having a desired rate of release. In these aspects, for example, the addition of an amount of anticancer agent that is less than necessary to bind higher affinity groups will provide a slower release, without an immediate release. In another example, an addition of anticancer agent in amount that is sufficient to saturate higher affinity groups will provide a faster release than the former example, because the anticancer agent is present in an amount sufficient to bind to additionally bind to lower affinity components, such as but not limited to, hydroxyls, amines and carboxyl groups, which will lead to a more immediate release.

In various embodiments, the one or more anticancer agents can elute or be released from the collagen construct over a period of time. The anticancer agent can elute or be released from the collagen construct continuously and/or substantially continuously over a period of time. "Substantially continuously," as used herein refers to a release of an anticancer agent all or part of the time such that on average the release of the anticancer agent still confers an overall beneficial effect on the subject.

Thus, there may be some short, intermittent and/or regular time periods in which an anticancer agent is not being released, but the overall beneficial effect of the anticancer agent on the subject remains. In some embodiments, the release rate of an anticancer agent can vary over a period of time and/or there can be multiple release rates of an anticancer agent. Alternatively, the release rate of an anticancer agent can be substantially constant (i.e., on average varying less than about 30%, 20%, 15%, 10%, or 5%) over a period of time.

In some embodiments, the release rate of a anticancer agent can be substantially constant for a period of a time and vary over another consecutive or nonconsecutive period of time and vice versa. In other embodiments, there can be periods of time in which no anticancer agent is released. The release of an anticancer agent, in some embodiments, can occur in random and/or sequential releases of the same or varying concentration. When there is more than one anticancer agent present in the collagen construct, the releases of the anticancer agents can overlap or the release rates can occur at different times. Further, when there is more than one anticancer agent present in the collagen construct, the release rates can be the same or the release rates can be different.

The collagen construct can have one or more release rates of an anticancer agent. For example, the collagen construct can have 1, 2, 3, 4, 5, or more release rates of an anticancer agent from the collagen construct. In certain embodiments, an NDGA-collagen construct comprising platinum, provided according to this invention, provides for two release rates of the platinum from the NDGA-collagen. In another embodiment, for the first release, after incubating the NDGA-collagen in normal saline at about 37° C. for about 1 day, about 25% of the total amount of platinum incorporated into and/or onto the NDGA-collagen is released from the NDGA-collagen. In another embodiment, over the course of the next 29 days, about 35% of the total amount of platinum incorporated into and/or onto the NDGA-collagen is released from the NDGA-collagen. Thus, in certain embodiments, after about 30 days, about 60% of the total amount of platinum incorporated into and/or onto the NDGA-collagen is released from the NDGA-collagen. Accordingly, about 40% of the total amount of platinum incorporated into and/or onto the NDGA-collagen remains bound to the NDGA-collagen after about 30 days.

The amount of an anticancer agent released from the collagen construct in the one or more releases over a period of time, e.g., about 1 minute to about 100 days.

The amount of an anticancer agent released from a collagen construct can be measured by standard procedures, such as, but are not limited to, quantitative chemical analytical and/or bioanalytical techniques such as atomic absorption spectroscopy, mass spectrometry such as inductively coupled plasma mass spectrometry (ICP-MS), gas chromatography, immunoassays, and/or any combination thereof.

To measure the amount of an anticancer agent released from a collagen construct, the construct can be placed in a saline solution at a specified temperature for a desired period of time. The saline solution can have an osmolarity of between about 100 mOsm/L to about 1000 mOsm/L or any range therein, such as between about 100 mOsm/L to about 500 mOsm/L or between about 250 mOsm/L to about 350 mOsm/L. In particular embodiments, the saline solution is normal saline. The temperature can be between about −80° C. to about 80° C. or any range therein, such as between about −80° C. and about −10° C., about −20° C. to about 15° C., about 5° C. and about 80° C., or about 30° C. and about 40° C. In particular embodiments, the temperature is about 37° C. The period of time can be any duration of time in which the amount of the anticancer agent released is desired to be known, such as about 15 minutes, about 1 hour, about 5 hours, about 1 day, about 5 days, about 30 days, about 100 days, or more. After which time the amount of the anticancer agent released into the saline can be measured, as described above, and subsequently the rate of release can be calculated. Alternatively, a sample (e.g., blood or urine) can be taken from the subject in which the construct is implanted and the sample can be analyzed using methods such as those described above.

To accelerate the test to determine the amount of an anticancer agent released from a collagen construct over a desired duration of time, such as the lifetime of the construct, an enzyme can be added to the saline solution. Exemplary enzymes include, but are not limited to, pepsin, bromelain, chymopapain, chymotrypsin, collagenase, ficin, papain, peptidase, proteinase A, proteinase K, trypsin, microbial proteases, and combinations thereof. In certain embodiments of the present invention, the enzyme is a collagenase. The amount of the one or more enzyme(s) added to the saline solution can be adjusted to accelerate the degradation of the collagen construct over a desired period of time. After the enzymatic degradation of the collagen construct for the desired amount of time, the amount of the anticancer agent released into the saline can be measured, as described above, and subsequently the rate of release can be calculated.

In other aspects, the release of an anticancer agent from the collagen construct can allow for the collagen construct to retain its ability to kill and/or inhibit microorganisms (e.g., bacteria, viruses, etc.) over an extended period of time. Thus, the collagen construct can provide a sustained anticancer effect.

In some embodiments of the present invention, the collagen construct has at least two different rates of release of at least one anticancer agent from the collagen construct. The two different rates of release can be of the same anticancer agent or of two or even more anticancer agents. In other embodiments of the present invention, the collagen construct has at least three different rates of release of an anticancer agent from the collagen construct. The three different rates of release can be of the same anticancer agent or of two or more anticancer agents.

In one aspect, the collagen construct can have an initial release of an anticancer agent from the collagen construct. The initial release of the anticancer agent can be a short-term and/or an "immediate" bolus release of the anticancer agent from the collagen construct after implantation. The amount of an anticancer agent released from the collagen construct in the initial release can be from about 1% to about 40% or any range therein, such as about 10% to about 30%, about 15% to about 35%, or about 20% to about 30% of the total amount of an anticancer agent incorporated into and/or onto the collagen construct from about 1 minute to about 1 day or any range therein, such as between about 15 minutes to about 20 hours or between about 30 minutes to about 15 hours after implantation. In particular embodiments, about 20% to about 30% of the total amount of an anticancer agent incorporated into and/or onto the collagen construct is released after about 1 day after implantation.

In another aspect, the collagen construct can have a second and/or an intermediate release of an anticancer agent from the collagen construct. The intermediate release can provide for a prolonged release, in comparison to the immediate release described above, of the anticancer agent from the collagen construct and can allow for the collagen construct to retain its ability to kill and/or inhibit microorganisms (e.g., bacteria, viruses, etc.) over an extended period of time. The amount of an anticancer agent released from the collagen construct in the second release can be from about 20% to about 100% or any range therein, such as about 25% to about 75% or about 30% to about 40% of the total amount of an anticancer agent incorporated into and/or onto the collagen construct from about 1 day to about 60 days or any range therein, such as between about 1 day to about 30 days or between about 1 day to about 20 days after implantation. In certain embodiments, about 30% to about 40% of the total amount of an anticancer agent incorporated into and/or onto the collagen construct is released after about 30 days after implantation.

In other aspects, after about 30 days after implantation, about 30% to about 100% or any range therein, such as about 30% to about 70%, or about 35% to about 50% of the total amount of an anticancer agent incorporated into and/or onto the collagen construct can remain incorporated into and/or onto the collagen construct. In certain embodiments, about 30% to about 100% or any range therein, such as about 30% to about 70%, or about 35% to about 50% of the total amount of an anticancer agent incorporated into and/or onto the collagen construct can be released from about 30 days to about 100 days after implantation, about 30 days to about 3 years after implantation, or for the rest of the useful lifetime of the collagen construct.

In further aspects, the collagen construct can have a third and/or extended release of an anticancer agent from the collagen construct. The intermediate release can provide for a prolonged release, in comparison to the immediate and/or intermediate release described above, of the anticancer agent from the collagen construct. In some embodiments of the invention, a portion and/or the remainder of an anticancer agent, e.g., platinum, incorporated into and/or onto the collagen construct can be released or eluted from the collagen construct as it breaks down, absorbs, delaminates, denatures, etc. The amount of the anticancer agent released from the collagen construct as it breaks down, absorbs, delaminates, denatures, etc. can be from about 30% to about 100% or any range therein, such as about 30% to about 70%, or about 35% to about 50% of the total amount of an anticancer agent incorporated into and/or onto the collagen construct.

The anticancer agent, e.g., platinum, can be released at a substantially constant release rate from the collagen construct or at one or more different release rates from the collagen construct over a period of time. In particular embodiments, the anticancer agent is released at least three different rates over time. For example, about 15% to about 35% of the total amount of an anticancer agent incorporated into and/or onto a collagen construct can be released or eluted from the collagen construct after about 1 day after implantation and about 50% to about 70% of the total amount of an anticancer agent incorporated into and/or onto a collagen construct can be released after about 30 days after implantation. The remainder of the anticancer agent present in the collagen construct or a portion thereof can be released for the rest of the lifetime of the collagen construct and/or as it breaks down, absorbs, delaminates, denatures, etc. at a constant rate, a variable rate, an intermittent rate, or any combination thereof. In particular embodiments, a release of an anticancer agent is a therapeutically effective amount of the anticancer agent.

In certain aspects, the invention relates to a biocompatible cross-linked collagen construct comprising a collagen construct that is modified so as to bear multiple quinone and/or catechol groups, to which anticancer agents, such as platinum, can bind with affinity. In these aspects, the cross-linked collagen construct is in one respect an affinity based carrier for which one may use commonly understood techniques relating to equilibrium constants to control the level of anticancer agent that binds to the cross-linked collagen construct, in order to effect particular desired release rates. In this regard, the binding affinity of platinum to collagen constructs can be adjusted as needed using several techniques. For example, the binding affinity can be adjusted by modifying the amount of cross-linking agent (e.g. NDGA) that is reacted with the collagen. In another example, one or more oxidizing and/or reducing agents can be used to modify and/or change the oxidation state of a functional group present in the cross-linked collagen construct, thereby altering the binding affinities of the anticancer agent for the cross-linked collagen construct. In this regard, the anticancer binding affinities, referred to hereinabove as having at least three affinity phases, can be altered depending on the desired rate of release. Accordingly, in certain aspects, a variety of release rates can be achieved.

Particular embodiments of the present invention provide a method of treating and/or preventing a disease and/or clinical symptom comprising: a) implanting a construct of the present invention in a subject, wherein the construct comprises collagen and an anticancer agent incorporated into and/or onto the construct to provide a total amount of the anticancer agent in the construct, and b) releasing or delivering the anticancer agent in a plurality of in vivo releases. The collagen of the construct can comprise natural collagen and/or synthetic collagen in any form. In some embodiments of the present invention, the collagen comprises at least one elongate synthetic collagen fiber, more typically a plurality of elongate synthetic collagen fibers.

In particular embodiments, after implantation of the construct in a subject, the construct delivers a therapeutically effective amount of the anticancer agent in one or more in vivo releases of the anticancer agent from the construct. In other embodiments, the plurality of in vivo releases, as measured in a saline solution at 37° C., comprise a first release (R1) from $t=0$ to $t=$ about 1 day after implantation and a second release (R2) from $t=$ about 1 day to $t=$ about 30 days after implantation. In some embodiments of the present invention, the anticancer agent is an anticancer agent, such as platinum, that is used to treat and/or prevent and/or inhibit cancer.

FIG. 1 is a flow chart of operations that can be used to carry out embodiments of the present invention. The one or more anticancer agents can be incorporated into and/or onto the collagen constructs of the present invention at any time after a collagen construct (e.g., collagen fiber or a device with such fibers) is provided (block 500). In some embodiments of the present invention, the anticancer agent is incorporated into and/or onto a collagen fiber of the collagen construct before it is formed. In other embodiments, the anticancer agent is incorporated into and/or onto a collagen fiber of the collagen construct after it is formed into a pre-final or final configuration/shape.

The anticancer agent can be incorporated into and/or onto a collagen construct during and/or after polymerization of a collagen fiber in the construct with a suitable cross-linker, such as, for example, NDGA (block 510). The amount of cross-linker present in the collagen construct can be less than about 15%, typically between about 10% to about 1%, such as between about 5% to about 1%. In particular embodiments of the present invention, the amount of cross-linker, e.g., NDGA, present in the collagen construct is less than about 15%, 14%, 13%, 12%, 11%, 10%, 9%, 8%, 7%, 6%, 5%, 4%, 3%, 2%, 1%, or any other range therein. Accordingly, the amount of collagen present in the collagen construct can be more than about 85%, typically between about 90% to about 100%, such as between about 90% to about 95%. In particular embodiments, the amount of collagen in the collagen construct is more than about 85%, 86%, 87%, 88%, 89%, 90%, 91%, 92%, 93%, 94%, 95%, 96%, 97%, 98%, 99%, or any other range therein: In some embodiments, the amount of polymerized collagen is increased to increase the amount of an anticancer agent incorporated into and/or onto a collagen construct. The collagen construct can further comprise non-collagenous components or biocompatible materials, such as particulates, hydroxyapatite and other mineral phases, or drugs that facilitate tissue growth or other desired effects. See, U.S. Pat. No. 6,821,530, the contents of which are incorporated herein by reference above.

The cross-linking agent can be any suitable polymerizing (i.e., cross-linking) material, such as, but not limited to, NDGA, 3,4-dihydroxyphenylalanine, dopamine, 3,4-dihydroxybenzaldehyde, 3,4-dihydroxybenzoic acid, carbodiimide, glutaraldehyde, formaldehyde, tannic acid, isocyanates, and epoxy resins. In other embodiments, the cross-linking agent can be any suitable polymerizing material in which at least one reactive group of the peptide is part of a diamino acid, such as but not limited to, lysine, arginine, asparagine, cysteine, glutamine, histidine and ornithine. In these aspects, hydroxyl groups and mercapto groups on the peptide may contribute to the cross-linking reaction. In other aspects, a dicarboxylic acid may be used as the cross-linking agent, thereby introducing a hydrocarbon bridge in-between the cross-linked sections having a free amino, hydroxyl or thiol group. In particular embodiments, the cross-linking agent comprises a quinone group and/or a catechol group. Exemplary cross-linking agents that can comprise a quinone and/or catechol functional group include, but are not limited to NDGA, 3,4-dihydroxyphenylalanine, and dopamine. Thus, the polymerized collagen can comprise one or more quinone and/or catechol groups. In certain embodiments, the cross-linking agent is selected based on the anticancer agent(s) desired to be incorporated into and/or onto the collagen construct. For example, when platinum is desired as an anticancer agent, a cross-linking agent that comprises a quinone and/or catechol functional group, e.g., NDGA, or that comprises one or more basic nitrogen atoms, is selected.

Once an anticancer agent is provided (block 550), the collagen construct can be contacted with an anticancer agent to incorporate the anticancer agent into and/or onto the collagen construct (block 580). The collagen construct can be contacted with an anticancer agent via a loading solution (i.e., a solution comprising the anticancer agent) for a period of time sufficient to allow for the anticancer agent to be incorporated into and/or onto the construct. Alternatively and/or in addition to contacting the collagen construct with a loading solution, the collagen construct can be contacted with a powder, such a dry powder comprising an anticancer agent. The term "contacting" as used herein in reference to the incorporation of the anticancer agent into and/or onto the construct, is intended to include treating, soaking, suspending, immersing, saturating, dipping, wetting, rinsing, washing, submerging, emersing, spraying, rolling, and/or any variation and/or combination thereof. The construct can be contacted with an anticancer agent for a period of time of about 1 minute to about 24 hours or more. In some embodiments, the contacting step can be carried out for a period of time of about 1 minute to about 36 hours or any range therein, such as about 1 hour to about 24 hours or about 10 hours to about 20 hours. After being contacted with the one or more anticancer agents, the construct can be washed with water and/or a suitable buffer. The buffer can be any buffer, including, but not limited to, for example, sodium acetate, 4-(2-hydroxyethyl)-1-piperazineethanesulfonic acid (HEPES), or 3-(N-morpholino) propanesulfonic acid (MOPS) at a pH of about pH 6.5 to about 7.8. The pH of the buffer can be about 6.5, 6.6, 6.7, 6.8, 6.9, 7.0, 7.1, 7.2, 7.3, 7.5, 7.4, 7.6 or 7.8. The collagen construct can then be dried.

The contacting step can be carried out at a temperature between about 5° C. to about 80° C. or any range therein, such as between about 10° C. and about 60° C., about 15° C. to about 40° C., or about 20° C. and about 30° C. In particular embodiments, the temperature is about 25° C. The contacting step can be carried out at atmospheric pressure, reduced pressure (e.g., vacuumized pressure), high pressure, and/or any combination thereof. In particular embodiments, the pressure is atmospheric pressure.

The amount of an anticancer agent incorporated into and/or onto the collagen constructs of the present invention can be influenced by varying different factors in the method of incorporating the anticancer agent. For instance, whether there are more than one anticancer agents in the loading solution can affect the amount of an anticancer agent incorporated into the collagen construct. The concentration of the one or more anticancer agents in the loading solution can also affect the amount of an anticancer agent incorporated into the collagen construct. The concentration of the one or more anticancer agent in the loading solution can range from about 0.1% to about 50%, such as about 0.5% to about 35% or about 1% to about 20%. In particular embodiments, the concentration of an anticancer agent in the loading solution is about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or any other range therein. In some embodiments of the present invention, the concentration of an anticancer agent in the loading solution is from about 0.1% to about 5%. In other embodiments, the loading solution can be a saturated or a supersaturated solution of the solute, i.e., the anticancer agent.

The pH of the loading solution as well as any additional components in the loading solution can influence the amount of an anticancer agent that is incorporated in the collagen construct. In some embodiments, the pH of the loading solution is between about pH 3-9, such as about pH 3, 4, 5, 6, 7, 8, 9 or any other pH value therein. Additional components in the loading solution can include, but are not limited to, agents that aid with the incorporation of the anticancer agent into and/or onto the collagen construct, agents that modify the collagen construct such as oxidizing agents and reducing agents, agents that aid with the solubility of the anticancer agent, agents that modify the pH of the loading solution, and any combination thereof. Further, other anticancer agents, non-collagenous components or biocompatible materials, such as particulates, hydroxyapatite and other mineral phases, or drugs that facilitate tissue growth or other desired effects can be present in the loading solution. See, U.S. Pat. No. 6,821, 530, In certain embodiments of the present invention, the collagen construct is contacted with an agent that modifies the collagen construct (block 520). The agent can aid in incorporating an anticancer agent into and/or onto the collagen construct by increasing the amount of the anticancer agent bound and/or the enhancing and/or strengthening chemical bond between the anticancer agent and the collagen construct. The modifying agent can alter a functional group present in the collagen construct to increase and/or enhance the incorporation of an anticancer agent into and/or onto the collagen construct. In some embodiments, the modifying agent can change the oxidation state of a functional group present in the collagen construct. In these embodiments, reducing and/or oxidizing agents may be used to by one of ordinary skill in the art to modify and/or change the binding affinity of the anticancer agent for the collagen construct. In particular embodiments, a functional group present in the collagen construct is modified to be a quinone group or a catechol group. The modifying agent, in other embodiments, blocks (e.g., partially or completely) a functional group present in the collagen construct. Blocking, and optionally later unblocking a functional group, can allow for one or more anticancer agents and/or other materials to be incorporated into and/or onto the collagen construct.

The method of incorporating an anticancer agent into the collagen constructs of the present invention can be repeated to add more of the same anticancer agent and/or to add one or more additional anticancer agents.

II. Exemplary Collagen Construct

The collagen constructs of the present invention comprise collagen, typically dermal collagen. However, the collagen can be of any form and from any origin. The collagen can be any of the identified collagen genotypes, for example, the interstitial fiber forming collagen types I, II and III, as well as any other substantially fiber forming types of collagen, for example collagen VI. The collagen can be acid soluble collagen or pepsin solubilized or soluble collagen. The collagen can be from mammalian cells synthesized in vitro. The collagen can be from molecularly engineered constructs and synthesized by bacterial, yeast or any other molecularly manipulated cell type. For example, the collagen can be sea cucumber dermis collagen, bovine, caprine, porcine, ovine or other suitable donor mammal, marine animal collagen such as chinoderms, molecularly engineered collagen, or gelatin (e.g., in any suitable form including solid, gel, hydrogels, liquids, or foams). In addition, the collagen can be digested with a protease before, where used, oxidizing and polymerizing steps. The collagen can be in the form of microfibrils, fibrils, natural fibers, or synthetic fibers.

In some embodiments, the collagen can be solubilized, dissolved or otherwise transferred into an acid solution, for example, acetic acid (e.g., about 0.01 M to about 1.0 M, typically about 0.5 M), hydrochloric acid (between about pH 1 to about pH 3, typically about pH 2.0), or any other suitable acid at appropriate concentration (e.g., about pH 1.0 to about pH 3.0, typically about pH 2.0). Dialysis may optionally be used to neutralize a soluble collagen solution. The collagen can also or alternatively be dissolved in a neutral buffered solution either with or without salts, e.g., phosphate buffer at about pH 7.0, or phosphate buffered saline at about pH 7.0. The phosphate buffer can be at any concentration of sodium phosphate between about 0.01 M and about 0.5 M, but more typically between about 0.02 M and about 0.1M. The buffer can also be any buffer, including, but not limited to, for example, sodium acetate, 4-(2-hydroxyethyl)-1-piperazineethanesulfonic acid (HEPES), or 3-(N-morpholino) propanesulfonic acid (MOPS). The collagen can be present in a quantity that is at least about 0.1% to about 10%, typically between about 0.1% to about 5% (e.g., about 0.1, 0.2, 0.3, 0.4, 1.0, 2.0, 4.0%) weight per volume, or weight per volume in the neutral buffer solution before fibrillogenesis and fiber formation. In a dried fiber collagen, collagen can be present in an amount of weight by volume of between about 50-100% (e.g., at least about 75%, 90%, 95% or 100%) before crosslinking (where crosslinking is used).

Collagen "microfibrils," "fibrils," "fibers," and "natural fibers" refer to naturally-occurring structures found in a tendon. Microfibrils are about 3.5 nm to about 50 nm in diameter. Fibrils are about 50 nm to about 50 μm in diameter. Natural fibers are above about 50 μm in diameter. A "synthetic fiber" refers to any fiber-like material that has been formed and/or chemically or physically created or altered from its naturally-occurring state. For example, an extruded fiber of fibrils formed from a digested tendon is a synthetic fiber but a tendon fiber newly harvested from a mammal is a natural fiber.

Of course, synthetic collagen fibers can include non-collagenous components or biocompatible materials, such as particulates, hydroxyapatite and other mineral phases, or drugs that facilitate tissue growth or other desired effects. See, U.S. Pat. No. 6,821,530, incorporated herein by reference above. For example, the fibers and/or constructs formed from same, can include compositions that can contain carbon nano-tubes, zinc nano-wires, nano-crystalline diamond, or other nano-scale particulates; and larger crystalline and non-crystalline particulates such as calcium phosphate, calcium sulfate, apatite minerals. For example, the compositions can also or alternatively contain anticancer agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, decorin, fibromodulin, COMP, elastin, and fibrillin. In some embodiments, the fibers and/or fiber-derived constructs can contain cells, engineered cells, stem cells, and the like. Combinations of the above or other materials can be embedded, coated and/or otherwise directly or indirectly attached to the collagen fibers and/or construct formed of same.

The term "collagen gel" means a semi-solid (e.g., gelatinous density) material that includes collagen fiber, fibrils and/or microfibrils, typically dermal collagen, that has been acid or pepsin solubilized (e.g., soluble collagen) and processed to maintain the collagen in its molecular form. The collagen concentration of the soluble collagen and/or resulting soluble collagen gel can be between about 0.1% to about 4% weight per volume. The collagen can be solubilized, dissolved, and/or suspended in a solution (e.g., water or buffer solution). The solution can be a neutralized solution with a pH of about pH 7.0 to about 7.4. The pH can be about 7.0, 7.1, 7.2, 7.3, or 7.4. In some embodiments the pH is about 7.2. The buffer can be any buffer, including, but not limited to, for example, sodium acetate, 4-(2-hydroxyethyl)-1-piperazineethanesulfonic acid (HEPES), or 3-(N-morpholino) propanesulfonic acid (MOPS) at a pH of about pH 7.0 to about 7.4. The soluble collagen gel may be formed to be in a cylindrical shape of a defined length and diameter, typically with a diameter of between about 0.1 cm to about 1 cm, and a length of between about 5 cm to about 100 m, more typically between about 1 m to about 50 m.

The collagen gel can comprise non-collagenous components or biocompatible materials, such as one or more particulates and/or minerals. Exemplary minerals include, but are not limited to, calcium phosphate, calcium hydrogen phosphate, calcium dihydrogen phosphate, monotite, brushite, calcium pyrophosphate, tricalcium phosphate, tetracalcium phosphate, octacalcium phosphate, amorphous calcium phosphate, hydroxyapatite, carbonateapatite, calcite, and calcium sulfate. One or more minerals can be present in a quantity from about 0.1% to about 5%, typically between about 0.1% to about 1% (e.g., 0.1, 0.2, 0.4, 0.6, 0.8, or 1%) weight per volume. When one or more minerals and/or particulates are present in the collagen gel, the collagen gel can be used to create a rough or textured surface. "Rough" as used herein refers to an unequal or varied surface that can contain surface texture, ridges, and/or bumps. In some embodiments at least one mineral is present in the collagen gel to create a rough inner and/or outer surface. The higher the mineral concentration in the collagen gel, typically, the rougher the surface and/or resulting tube. A high mineral concentration can provide a surface and/or a tube that is lighter in color than a surface and/or tube containing no minerals.

The collagen fibers and collagen gel can be produced in batch or continuous-type systems, including wet gel collagen extrusion systems, which produce cylindrical lengths of gel that can be allowed to substantially dry (actively or passively) to obtain a suitable length of fiber. Examples of some collagen fiber production processes that can generate soluble collagen in suitable lengths are described in U.S. Pat. No. 6,565,960, and pending U.S. Patent Application Publication No. US-2008-0188933-A1, the contents of which are hereby incorporated by reference.

The collagen fibers can be spooled for supplying to an automated or semi-automated winder to form the biomedical construct. The collagen fibers may be formed with a relatively thin diameter, such as, for example between about 0.05 mm to about 0.2 mm (average), such as about 0.08 mm dry diameter (average) and about a 0.13 mm wet diameter (average). A collagen fiber can be an elongate continuous length of fiber formed of denatured (gelatin) and/or non-denatured collagen (e.g., whole or fragmented native collagen fibers from tendon, skin, or other sources). The fiber can have a length of at least about 0.25 inches, typically greater than about 0.5 inches, such as between about 1-30 inches or between about 1 m to about 100 m. In certain embodiments of the present invention, a plurality of elongate collagen fibers can be utilized. In particular embodiments of the present invention, an elongate collagen fiber is polymerized before and/or after it is used to prepare a construct.

The term "gelatin" refers to denatured collagen. Gelatin can be derived from collagen in a well known manner or can be obtained from commercial suppliers, such as Sigma-Aldrich®, located in St. Louis, Mo. An exemplary method of obtaining gelatin is by heating collagen at a suitable temperature to cause it to become denatured. Denaturation results in the irreversible transformation of collagen into a random coiled structure, which is gelatin. Gelatin can be derived from one or more sources of collagen and derived from one or more types of collagen, such as but not limited to, types I, II, III, and/or VI. Exemplary sources from which gelatin is derived include, but are not limited to, sea cucumber dermis collagen, bovine, caprine, porcine, ovine or other suitable donor mammal collagen, and marine animal collagen such as chinoderms. The gelatin can be derived from collagen obtained from mammalian cells synthesized in vitro. The gelatin can be derived from collagen obtained from molecularly engineered constructs and synthesized by bacterial, yeast or any other molecularly manipulated cell type.

The term "gelatin slurry" as used herein refers to a mixture of gelatin in a solvent (e.g., water or buffer solution). The gelatin slurry can be a homogeneous or heterogeneous mixture. Gelatin in the gelatin slurry can be suspended, solubilized, and/or dissolved (e.g., completely or partially) in a solvent to form a gelatin slurry. The gelatin slurry can comprise other components, such as, but not limited to, one or more minerals and/or particulates, that can be suspended, solubilized, and/or dissolved in the solvent. The buffer can be any buffer, including, but not limited to, for example, sodium acetate, 4-(2-hydroxyethyl)-1-piperazineethanesulfonic acid (HEPES), or 3-(N-morpholino) propanesulfonic acid (MOPS) at a pH of about pH 6.5 to about 7.8. The pH of the buffer can be about 6.5, 6.6, 6.7, 6.8, 6.9, 7.0, 7.1, 7.2, 7.3, 7.5, 7.4, 7.6 or 7.8. In some embodiments the pH is about 7.2. The gelatin can also or alternatively be dissolved in a neutral buffered solution either with or without salts, e.g., phosphate buffer at about pH 6.5 to about 7.8, or phosphate buffered saline at about pH 6.5 to about 7.8. The phosphate buffer can be at any concentration of sodium phosphate between about 0.01 M and about 0.5 M, but more typically between about 0.02 M and about 0.1 M. The gelatin can be present in a quantity from about 0.1% to about 60%, typically between about 2% to about 40% (e.g., about 2, 3, 4, 5, 6, 7, 8, 10, 15, 20, 25, 30, 35, or 40%) weight per volume.

The gelatin slurry can be heated to create a viscous slurry at a temperature that keeps the gelatin from gelling or solidifying during application, and/or to dissolve or solubilize the gelatin in the solvent. When a gelatin slurry is cooled to a sufficient temperature a "gelatin hydrogel" is formed. The term "gelatin hydrogel" as used herein refers to a semi-solid (e.g., gelatinous density) material formed by the gelatin slurry that includes gelatin and can comprise other components, such as, but not limited to, one or more minerals and/or particulates. The gelatin in the gelatin slurry and in the resulting gelatin hydrogel are composed of denatured collagen and cannot be used to produce collagen fibers, fibrils, and/or microfibrils. To be clear, in contrast, the term "collagen gel" as used herein refers to a gel that includes collagen fiber, fibrils and/or microfibrils that has been acid or pepsin solubilized (e.g., soluble collagen) and processed to maintain the collagen in its molecular form, whereas the terms "gelatin hydrogel" and "gelatin slurry" as used herein refer to compositions of gelatin, which is denatured collagen that cannot be used to produce collagen fibers, fibrils, and/or microfibrils. Stated differently, gelatin is denatured collagen which does not maintain collagen in its molecular form since it is irreversibly transformed into a random coiled structure.

The gelatin slurry and/or the gelatin hydrogel, which may or may not be attached to at least one collagen fiber, can be cross-linked with a suitable polymerizing (i.e., cross-linking) material, such as, but not limited to, NDGA, 3,4-dihydroxyphenylalanine, dopamine, 3,4-dihydroxybenzaldehyde, 3,4-dihydroxybenzoic acid, carbodiimide, glutaraldehyde, formaldehyde, tannic acid, isocyanates, and epoxy resins, or may be used in a non-cross-linked state. In particular embodiments, the cross-linker comprises a quinone group and/or catechol group. Exemplary cross-linking agents that can comprise a quinone and/or catechol functional group include, but are not limited to NDGA, 3,4-dihydroxyphenylalanine, and dopamine. Thus, the polymerized collagen can comprise one or more quinone and/or catechol groups.

Alternatively or in addition, the gelatin slurry and/or gelatin hydrogel can be stabilized with treatments, such as, but not limited to, one or more of dehydrothermal treatment, glycation, and ultraviolet light. The gelatin slurry and/or the gelatin hydrogel treated with a polymerizing material and/or a stabilization treatment can be resistant to liquification at 37° C. and/or thermally stable at temperatures over about 37° C. The gelatin slurry and/or the gelatin hydrogel treated with a polymerizing material and/or a stabilization treatment can be thermally stable at temperatures up to about 120° C., typically at temperatures between about 37° C. to about 104° C. The polymerized and/or stabilized gelatin hydrogel can be stronger and/or stiffer than an untreated gelatin slurry and/or gelatin hydrogel (e.g., an untreated gelatin hydrogel has a compressive stiffness of about 0.70 MPa, compared to about 4.71 MPa for NDGA-treated gelatin hydrogel). The polymerized and/or stabilized gelatin hydrogel can be nearly elastic under dynamic compression loads (e.g., rebounds substantially completely after compression to over 80%, while untreated gelatin hydrogels fracture when compressed to 80%). The polymerized and/or stabilized gelatin hydrogel can undergo large deformations without comprising its mechanical properties. According to some embodiments, the gelatin slurry and/or the gelatin hydrogel, if polymerized (i.e., cross-linked) and/or stabilized, can be polymerized and/or stabilized at any time either before, during, and/or after application and/or drying to at least one collagen fiber, where applied.

The gelatin slurry can be heated prior to application typically above room temperature, such as up to about 120° C. or even more. In some embodiments, the gelatin slurry can be heated and/or kept at between about room temperature and about 100° C., typically between about room temperature and about 70° C. to keep the gelatin from gelling or solidifying during application, and/or to dissolve or solubilize the gelatin and/or one or more minerals in the solvent.

During application of the gelatin slurry onto a construct (e.g., collagen fiber), the gelatin slurry can be heated above room temperature, such as between about 20° C. and about 70° C., between about 20° C. and about 60° C., typically between about 45° C. to about 55° C. to keep the gelatin from gelling or solidifying during application, and/or to dissolve or solubilize the gelatin and/or one or more minerals in the solvent.

The gelatin slurry can be heated by known methods and devices, such as, but not limited to, heating using a water bath, heating block, heating pad, solar or light source, microwave, or bunsen burner. The temperature to which the gelatin slurry is heated can depend on the concentration of gelatin and/or other components present in the slurry. Typically, if a high concentration of gelatin and/or other components is present in the gelatin slurry, then the gelatin slurry may need to be heated to a higher temperature to create a viscous slurry at a temperature that keeps the gelatin from gelling or solidifying during application, and/or to dissolve or solubilize the gelatin and/or other components in the solvent. Generally, the higher the concentration of gelatin in the slurry, the higher the temperature needed to create a viscous slurry at a temperature that keeps the gelatin from gelling or solidifying during application, and/or to dissolve or solubilize the gelatin in the solvent. However, other components present in the gelatin slurry, e.g., minerals, may affect the viscosity of the gelatin slurry, the temperature at which the gelatin slurry gels or solidifies, and/or the solubility of the gelatin and/or minerals in the solvent. Thus, the temperature to which the gelatin slurry is exposed or heated to can vary.

The term "film" refers to a thin layer of collagen gel, gelatin slurry (typically comprising one or more minerals), and/or gelatin hydrogel (typically comprising one or more minerals) that has dried. The collagen gel, gelatin slurry, and/or gelatin hydrogel can be actively and/or passively dried. Exemplary methods of drying the collagen gel, gelatin slurry, and/or gelatin hydrogel include, but are not limited to, air drying, drying under heat, or drying in an oven or dryer using conduction, convection, infrared/radiant, or radio frequency. The moisture content of the resulting collagen film and/or gelatin film can be less than about 25% by weight of the film, less than about 15% by weight of the film, but is typically less than about 5% by weight of the film to provide a state of the collagen film and/or gelatin film at a low moisture content.

Several layers of the collagen gel, gelatin slurry, and/or gelatin hydrogel can be applied or used to generate the desired film thickness or coverage. For example, between about 1-20 layers of collagen gel, gelatin slurry, or gelatin hydrogel can be applied to form a collagen film or gelatin film, typically between about 1-10 layers of collagen gel, gelatin slurry, or gelatin hydrogel can be applied to form a collagen film or gelatin film. In particular embodiments, between about 1-20 layers of collagen gel are placed about an outer surface of a support member and allowed to dry, then, at least one collagen fiber is wound a number of revolutions about a length of the support member and while winding the at least one collagen fiber between about 1-20 layers of a gelatin slurry are applied to the at least one collagen fiber and optionally allowed to dry, then, between about 1-20 layers of collagen gel are placed onto the at least one collagen fiber with the gelatin hydrogel or gelatin film and allowed to dry.

The one or more layers of collagen gel, gelatin slurry, and/or gelatin hydrogel can comprise different components and/or comprise the same components present in different concentrations. In certain embodiments, each of the layers comprise the same components, e.g., minerals and particulates, and in other embodiments the layers comprise different components. In particular embodiments, each of the layers comprise the same components, but in each layer the concentration of the components is different. For example, in certain embodiments, the mineral concentration in a first (inner) layer can be less than the mineral concentration in the outer layer. The film can be present in a thickness that is between about 5 microns and about 1 mm, typically between about 5 microns and about 700 microns, and more typically between about 5 microns and about 500 microns. The film of gelatin hydrogel is typically thicker than the film of collagen gel.

In some embodiments, a collagen gel, where used, can provide a smooth (and typically a substantially constant diameter) surface over and/or under the at least one collagen fiber. In other embodiments, a collagen gel comprising one or more minerals, e.g., hydroxyapatite, where used, can provide a rough layer (e.g., inner and/or outer surface) over and/or under the at least one collagen fiber.

Methods of Treatment

Spectroscopic and chromatographic methods are employed to determine the solution stability of the constructs provided herein. The complexes are screened against, e.g., the L1210 mouse tumor model to determine antitumor activity. In addition the M5076 ovarian, H460 lung, B16 melanoma, and Lewis lung murine tumor models may be used, e.g., as xenografts.

When used as antitumor agents, the platinum complexes of this invention can be administered in a manner and with a protocol comparable to cisplatin, carbopatin, oxaliplatin, and/or satraplatin. They advantageously are administered to patients, humans or animals, having tumors susceptible to therapeutic treatment by platinum complexes, as sterile aqueous solutions. The solutions are preferably administered intraveneously or intraarterially, although other forms of administration may be indicated in certain cases. Solutions for intravenous injections will normally be sterile physiological solutions, which may also contain appropriate amounts of alkali, sodium bicarbonate, to convert complexes bearing acidic water-solubilizing groups to their salts. Suitable dosage forms can also include oily or aqueous injectable preparations, for intramuscular or intraperitoneal injection, and solid dosage forms, such as solid implants, capsules, and the like.

The effective amounts of the complex of the invention which should be administered can be determined by conventional methods which will be apparent to the skilled artisan. Normally, the activity of the platinum complex of this invention will be evaluated in a screen along with a known complex such as ciplatin, carboplatin, oxaliplatin, and/or satraplatin. The relative potency and the therapeutic index, the ratio of therapeutic effectiveness to toxicity, compared to that of the known analogue will normally determine the relative dosage compared to conventional dosages of the analogue for the type of cancer being treated.

The treatment regimen can be varied in ways which are well known to the skilled artisan, as a function of the type of cancer being treated, the condition of the subject, and the particular properties of the antitumor platinum complex being administered. Inevitably, a certain amount of experimentation is required to determine the optimum dosages and treatment regimens, as is normally the case for anticancer therapy.

The present invention is explained in greater detail in the following non-limiting Examples.

EXAMPLES

In the following examples certain collagen fiber constructs are utilized. Such constructs (e.g., sleeves or tubes) are cross-linked with nor-dihydroguaiaretic acid (NDGA). However, this cross-linking agent is only illustrative. The present invention is not intended to be limited to cross-linked constructs where NDGA is the cross-linking agent. For example, other cross-linking agents, such as, but not limited to 3,4-dihydroxyphenylalanine, dopamine, 3,4-dihydroxybenzaldehyde, 3,4-dihydroxybenzoic acid, a carbodiimide, glutaraldehyde or other di- and multi aldehydes, formaldehyde, tannic acid, isocyanates such as di- and multi-isocyanates, di and multi-diazopyruvates, pluronics, and epoxy resins, and/or stabilization treatments, such as, but not limited to, one or more of dehydrothermal treatment, glycation, and ultraviolet light may be used in the present invention. In particular embodiments, the cross-linking agent comprises a quinone group and/or catechol group. Thus, the polymerized collagen can comprise one or more quinone and/or catechol groups.

Example 1

Figure 2:
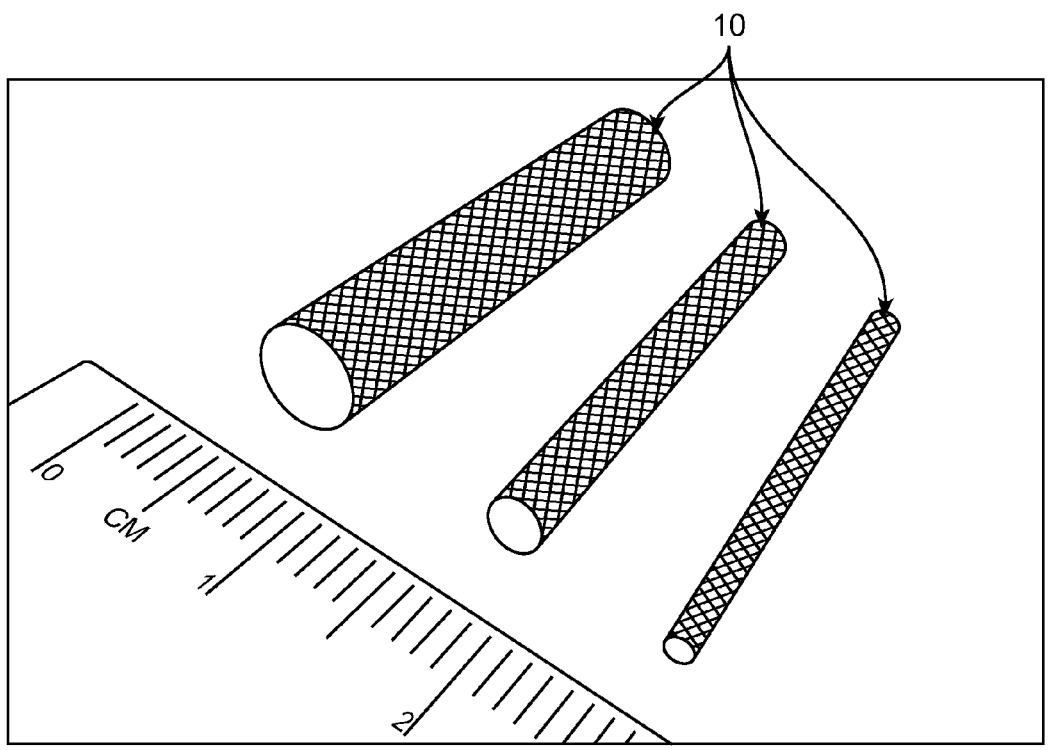
FIG. 2 is a digital photograph of exemplary NDGA-collagen tubes (10) according to embodiments of the present invention of varying diameter and length.

FIG. 2 illustrates exemplary sleeves or tubes (10) of wound NDGA-collagen fibers that may be particularly suitable for medical constructs. The NDGA-collagen tubes comprise a solid sheet of type I collagen cross-linked with NDGA (nor-dihydroguaiaretic acid) and can be prepared as described below in the materials and methods. The material can comprise greater than about 95% collagen and less than about 5% NDGA polymer. The diameter, length, and wall thickness of the collagen construct is scalable (FIG. 2). For instance, the inner diameter of the tube can vary between about 1 and 10 mm. The thickness of the wall can vary between about 0.1 and 3 mm. The length of the tube can vary, e.g., from between about 1 to 6 cm or more.

The mechanical properties of the NDGA-collagen constructs are governed by fiber angle, wall thickness (wall thickness/diameter) and cross-link density; all of which can be tuned to satisfy the mechanical requirements for the specific surgical application. NDGA-collagen is biocompatible and biodegradable. Biologically active compounds can be incorporated into the biomaterial, including hydroxyapatite and TCP minerals, extracellular matrix macromolecules (glycosaminoglycans), anticancer agents such as platinum and bisphosphonates, anti-inflammatory drugs, and antibiotics.

It in contemplated that platinum can be incorporated into NDGA-collagen constructs and that the platinum in the NDGA-collagen constructs can slowly elute from the construct in normal saline. Without being bound to any particular theory, platinum is believed to bind to and/or complex with the NDGA-collagen due to the high concentration of catechols/quinones and catechol/quinone derivatives in the cross-linked collagen material. NDGA contains two catechols which, without being bound to any particular theory, are contemplated to be responsible for cross-linking the collagen material through the generation of quinones and covalent adduct formation. Quinones have been demonstrated to bind transition and heavy metals. Biological materials that contain concentrated catechols/quinones can exhibit extraordinarily high affinity for metals and in some cases can be considered metal chelating compounds (e.g., siderophores).

Materials and Methods

NDGA-collagen tubes (10) 8×25 mm are manufactured as described in U.S. pending U.S. Patent Application Publication No. 2010/0094318, which is incorporated herein by reference, using purified type I bovine collagen. The tubes (10) are within engineering specifications of the product (weight and dimensions—weight: about 100 mg, dimensions: about 8 mm in diameter and about 25 mm long). The dried tubes (10) are incubated in 1% (w/v) platinum (II) diaqua complex in water at room temperature for 16 hours. The tubes are then washed with deionized water and dried. Platinum content in the NDGA-collagen is measured e.g., by Inductively Coupled Plasma-Mass Spectrometry (ICP-MS). Results are expressed as µg/g, which is equivalent to parts per million (ppm).

Strength of Binding

The strength of platinum binding in NDGA-collagen material comprising platinum, is evaluated by washing the material in increasing concentrations of a platinum chelator such as ammonium hydroxide or an alkylene diamine such as ethylene diamine. The samples are washed thoroughly with water, then incubated at the indicated platinum chelator concentrations. The amount of platinum remaining in the material is measured.

Platinum Elution in Normal Saline

NDGA-collagen tubes comprising platinum are incubated in normal saline at 37° C. for 1, 3, 6, 13 and 30 days. At each time point, six samples are collected, dried and the amount of platinum remaining in the material is measured.

Example 2

Platinum Binding in NDGA Cross-Linked Collagen Materials

To assess platinum binding in other NDGA cross-linked collagenous materials, samples of type I collagen fiber, bovine pericardium, porcine small intestinal submucosa (SIS), bovine tendon collagen sponge, bovine collagen casing, and plain gut suture are treated with NDGA according to established protocols, such as those described in U.S. Pat. No. 6,565,960, Koob, T. J. and Hernandez, D. H. "Material properties of NDGA polymerized collagen fibers: Development of biologically-based tendon constructs" Biomaterials, 23, 203-212 (2002), and Koob, T. J. and Hernandez, D. H. "Mechanical and thermal properties of novel polymerized NDGA-gelatin hydrogels" Biomaterials 24, 1285-1292 (2002), which are incorporated herein by reference. The NDGA treated materials are incubated in 1% (w/v) platinum (+2) diaqua complex as described in Example 1, washed with de-ionized water, and dried. Platinum content in the collagenous materials is measured on six replicate samples from each collagenous material. It is contemplated that the methods used to incorporate platinum into and/or onto the collagenous materials can be used on essentially any collagen based biomaterial.

The incorporation of platinum in collagenous materials can produce a biomaterial imbued with anticancer capabilities. As such, the method of incorporating platinum into collagenous materials can provide a drug delivery device, preferably for anticancer drug delivery.

Example 3

Weight Measurement and Metal Analysis of Exemplary Constructs

To determine the amount of platinum that can bind to gut sutures of various lengths and thicknesses, weight measurements and metal analysis are conducted as follows:

Materials

The following specimens are evaluated as follows:
a. Size 2-0 Plain Gut Sutures
b. Size 2-0 Plain Gut Sutures doped with platinum
c. Size 2-0 NDGA-crosslinked 24 hrs Gut Sutures
d. Size 2-0 NDGA-crosslinked 24 hrs Gut Sutures doped with platinum
e. 16-fiber braided NDGA-crosslinked collagen yarn (15 picks/inch, manufactured by Steeger USA, Inman, S.C.).

Each specimen evaluated is 60 mm long, and two specimens are evaluated for each group.

Metal Analysis

Three groups of specimens are prepared as follows:
Group 1: 2-0 plain gut+ platinum
Group 2: 2-0 NDGA gut+ platinum
Group 3: 16-fiber yarn suture+ platinum
Furthermore, five specimens from each of the groups are evaluated, for which each specimen is 20 mm in length. The weight of each specimen is measured in CE using a 4-digit balance, and metal analyses are conducted pursuant to standard protocols.

Example 4

Stability Studies

The stability of the crosslinked collagen-Pt constructs are determined by measuring the ultraviolet spectra of the constructs in solution, run, e.g., at half-hour intervals. The decrease in absorbance with time is a measure of complex decomposition.

The foregoing is illustrative of the present invention and is not to be construed as limiting thereof. Although certain illustrative embodiments of this invention have been described, those skilled in the art will readily appreciate that many modifications of these are possible without materially departing from the novel teachings and advantages of this invention. Accordingly, all such modifications are intended to be included within the scope of this invention as defined in the claims. The invention is defined by the following claims, with equivalents of the claims to be included therein.

The invention claimed is:

1. An anticancer cross-linked collagen construct comprising:
   a cross-linked collagen comprising collagen and one or more entities which cross link collagen in said construct and
   an anticancer amount of platinum incorporated into the construct, wherein at least a portion of the platinum incorporated into the construct is incorporated by chelation to said entities.

2. The construct of claim 1, wherein at least one of the cross-linking entities comprises a 1,2-benzoquinone and/or a 1,2-dihydroxy phenyl moiety.

3. The construct of claim 1, where the platinum is chelated at least in part to the benzoquinone and/or the 1,2-dihydroxyphenyl moiety.

4. The construct of claim 1, wherein at least one of the cross-linking entities is selected from the group consisting of entities arising from cross-linking the collagen with nordihydroguaiaretic acid (NDGA), 3,4-dyhydroxyphenylalanine, dopamine, 3,4-dihydroxybenzaldehyde, 3,4-dihydroxybenzoic acid, and tannic acid.

5. The construct of claim 1, wherein at least one of the cross-linking entities is arising from cross-linking the collagen with NDGA.

6. The construct of claim 1, wherein the platinum comprises platinum (II) and/or platinum (IV).

7. The construct of claim 6 wherein the platinum comprises cis-$(NH_3)_2Pt(II)$,

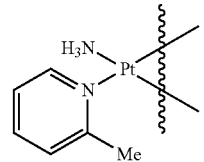

(II)

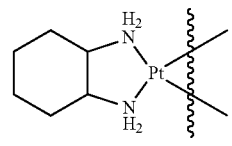

(II)

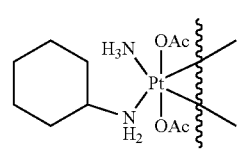

(IV)

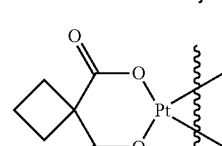

(II)

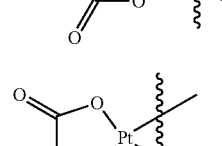

or (II)

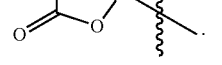
.

8. The construct of claim 1, wherein the platinum incorporated into the construct is present in an amount of between about 0.1% to about 30%.

9. The construct of claim 1, wherein some or all of the anticancer amount of platinum is released in vivo in contact with an aqueous medium.

10. The construct of claim 1, wherein the anticancer cross-linked collagen construct provides a sustained release of platinum, wherein the sustained release comprises a plurality of release rates including an immediate release, an intermediate release, an extended release or any combination of release rates thereof.

11. The construct of claim 10, wherein an effective amount of platinum is released from about 1 minute to about 60 days, or any range therein.

* * * * *